(12) United States Patent
Nahmad

(10) Patent No.: US 12,343,367 B1
(45) Date of Patent: Jul. 1, 2025

(54) PRESERVATION AND CLOSED-LOOP PROCESSING FOR OIL EXTRACTION OF FRESH PLANT MATERIALS

(71) Applicant: Eco-Logic Environmental Engineering Inc., Placentia, CA (US)

(72) Inventor: David Nahmad, Placentia, CA (US)

(73) Assignee: Eco-Logic Environmental Engineering Inc., Placentia, CA (US)

( * ) Notice: Subject to any disclaimer, the term of this patent is extended or adjusted under 35 U.S.C. 154(b) by 392 days.

(21) Appl. No.: 17/570,790

(22) Filed: Jan. 7, 2022

Related U.S. Application Data

(60) Provisional application No. 63/135,135, filed on Jan. 8, 2021.

(51) Int. Cl.

| | | |
|---|---|---|
| B01D 11/02 | (2006.01) |
| A01N 59/00 | (2006.01) |
| A61K 31/05 | (2006.01) |
| A61K 31/352 | (2006.01) |
| A61K 36/185 | (2006.01) |
| B01D 5/00 | (2006.01) |
| C07D 311/80 | (2006.01) |
| G01N 1/18 | (2006.01) |

(52) U.S. Cl.
CPC ............ *A61K 36/185* (2013.01); *A61K 31/05* (2013.01); *A61K 31/352* (2013.01); *B01D 5/006* (2013.01); *B01D 11/0207* (2013.01); *B01D 11/0219* (2013.01); *B01D 11/028* (2013.01); *B01D 11/0288* (2013.01); *B01D 11/0296* (2013.01); *A61K 2236/35* (2013.01); *A61K 2236/37* (2013.01); *A61K 2236/51* (2013.01)

(58) Field of Classification Search
CPC .............. A61K 2236/35; C07C 37/004; B01D 11/028; B01D 11/0273
USPC .................. 424/725, 774; 549/390; 436/177; 422/255, 261
See application file for complete search history.

(56) References Cited

U.S. PATENT DOCUMENTS

| | | | |
|---|---|---|---|
| 9,950,976 B1 | 4/2018 | Keller | |
| 2006/0074254 A1* | 4/2006 | Zhang | B01J 20/08 549/510 |

FOREIGN PATENT DOCUMENTS

| | | |
|---|---|---|
| CN | 110283048 A | 9/2019 |
| WO | 2017184642 A1 | 10/2017 |
| WO | 2019020738 A1 | 1/2019 |

OTHER PUBLICATIONS brinstrument.com Blog "Winterization and Filtration of cannabis extracts" https://brinstrument.com/blog/ pp. 1-12.
HempHacker blog "Why winterization stabilizes hash oil extracts" Posted by, HempHacker on Sep. 21, 2015, pp. 1-9.

(Continued)

*Primary Examiner* — Monzer R Chorbaji
(74) *Attorney, Agent, or Firm* — Umberg Zipser LLP

(57) ABSTRACT

Devices, systems, and methods are presented that allow processing of fresh plant materials to produce a stabilized liquor that preserves various compounds in the liquor over extended periods of time. Contemplated systems and methods advantageously obviate the need for drying and prevent oxidative and other degradation of valuable components. Moreover, the systems and methods contemplated herein will form a liquor enriched in desired hydrophobic components and depleted of undesired hydrophilic components.

15 Claims, 2 Drawing Sheets

(56) References Cited

OTHER PUBLICATIONS

Luigi L. Romano et al "Cannabis Oil: chemical evaluation of an upcoming cannabis-based medicine", Cannabinoids, vol. 7, Issue 1, May 5, 2013 pp. 1-11, Department of Pharmacy, University of Siena, ItalyPlant Metabolomics group, Institute of Biology, Leiden University, The Netherlands.

\* cited by examiner

PRESERVATION AND CLOSED-LOOP PROCESSING FOR OIL EXTRACTION OF FRESH PLANT MATERIALS

This application claims priority to U.S. Provisional Patent Application with the Ser. No. 63/135,135, which was filed Jan. 8, 2021, and which is incorporated by reference herein.

FIELD OF THE INVENTION

The present disclosure relates to devices and methods of storing, preserving, and stabilizing plant materials for downstream extraction, especially as it relates to storage and stabilization of hemp and *Cannabis* plant materials, and particularly fresh plant materials.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In most circumstances where hemp and *Cannabis* are harvested to produce extracts containing various cannabinoids and other phytochemicals, whole plants are harvested and subsequently dried. Where desired, flowers or buds are manually removed and separately dried, or removed after the harvested plant is dried. As will be readily appreciated, the drying operation is not only time-consuming but also requires significant operational space and energy. In addition, the drying process will allow for microbial contamination, and the cannabinoids and other phytochemicals are subject to deterioration as the plant material dries. Such difficulties are further exacerbated where the plant materials were harvested in a moist or wet state (e.g., after rain). Even in the dried state, cannabinoids and other phytochemicals are subject to oxidation and other deleterious reactions that ultimately adversely affect extract quality and yield of cannabinoids and other phytochemicals. Therefore, currently known operations rely on immediate processing that most typically employs a drying step prior to extraction. As a consequence, harvest and extraction are generally tightly linked in time and so contribute to significant price changes due to changing supply and demand. Moreover, where processing or extraction are delayed, the quality of such extracts increasingly deteriorates.

Numerous extraction methods are known for cannabinoids and other phytochemicals and exemplary processes are described in U.S. Pat. No. 9,950,976, WO 2017/184642, WO 2019/020738A1, and *Cannabinoids* 2013; 1(1):1-11, among various other techniques. In further known processes, hash oil is stabilized by a winterization process as described in HempHacker (URL: https://hemphacker.com/why-winterization-stabilizes-hash-oil-extracts/). Unfortunately, despite the relatively large variety of methods of isolation and/or stabilization, all or almost all of these processes are performed with dried plant parts as the starting material or with crude extracts that were obtained from dried plant materials. Therefore, the same disadvantages as noted above still remain.

Thus, even though various extraction processes for plant materials are known in the art, all or almost all of them suffer from various disadvantages. Consequently, there is a need to provide improved compositions and methods that avoid one or more of the above noted problems.

SUMMARY OF THE INVENTION

Various devices, systems, and methods are presented that allow for storage of fresh plant materials such as *Cannabis* plant materials in a system that stabilizes a hydrophobic component or fraction (e.g., comprising cannabinoids and/or terpenoids) over extended periods without the need for drying, and that produces a liquor that is enriched in the hydrophobic component or fraction while being depleted with respect to a hydrophilic fraction of the plant materials (e.g., chlorophyll, flavonoids). Advantageously, the system and method significantly reduces, if not even avoids degradation the desired compounds, and so formed liquor can be processed in one or more downstream processes to produce a purified plant extract or purified desired compounds.

In one aspect of the inventive subject matter, the inventor contemplates a method of storing and processing plant materials that includes a step of providing a storage container that contains a hydrophobic solvent as a bulk solvent and a hydrophilic solvent as a top layer solvent disposed above the hydrophobic solvent. In another step, fresh plant materials are collected in a biomass container that is configured to allow the bulk solvent to enter into and exit from the biomass container, and the biomass container is submerged in the bulk solvent below the top layer solvent such that the fresh plant materials are in contact with the bulk solvent. In yet another step, the fresh plant materials are stored in the biomass container to allow a hydrophobic component or fraction to dissolve in the bulk solvent and to allow a hydrophilic component or fraction to dissolve in the top layer solvent.

The solvent in some embodiments is comprised of a non-flammable mixture of several compounds based on a halogenated hydrocarbons body (65% to 85%), a highly polar compound like R—OH (alcohol) or R—O—R" (ketone) (5% to 10%) to remove all water-soluble compounds and ether (R—O—R') in (7% to 18%). In further embodiments the hydrophobic solvent is or comprises methylene chloride, while the hydrophilic solvent is or comprises water. Preferably, the fresh plant materials comprise *Cannabis* plant materials or portions thereof, and the biomass container is configured as a closed mesh or wire basket, a bag with walls that are permeable to the bulk solvent, or a closed container with a plurality of openings that allow bulk solvent exchange. While not limiting to the inventive subject matter, the fresh plant materials are stored in the biomass container for at least 4 weeks, or at least 3 months, or at least 6 months. Typically, but not necessarily, the hydrophobic fraction will comprise cannabinoids and/or terpenoids, while the hydrophilic fraction may comprise chlorophyll and/or flavonoids.

Contemplated methods may further include a step of closing the storage container and applying a vacuum to a head space of the container. Where desired, contemplated methods may include a step of feeding recycled bulk solvent to the storage container during storage. In other embodiments, during storage, a step of removing bulk solvent from the storage container may be included, wherein the bulk solvent is enriched in the hydrophobic fraction. In yet a further optional step, the hydrophobic solvent may be removed from the bulk solvent and the removed hydrophobic solvent may be recycled back to the storage container. Additionally, it is contemplated that a portion of the top layer solvent may be removed during storage, which may be used to remove at least some of the water and/or hydrophilic components contained in the plant materials. As needed or desired, additional fresh plant materials may be added to the biomass container while the initial fresh plant materials are stored in the biomass container.

Viewed from a different perspective, the inventor also contemplates a method of stabilizing a hydrophobic fraction from fresh plant materials that comprises a step of placing in a container the fresh plant materials into a hydrophobic solvent, wherein the hydrophobic solvent is overlaid with a hydrophilic solvent to thereby reduce or entirely eliminate evaporation and loss of the hydrophobic solvent. The fresh plant materials are then stored in the container to allow at least some of the hydrophobic fraction to dissolve in the bulk solvent and to allow at least some of a hydrophilic fraction from the fresh plant materials to dissolve in the hydrophilic solvent. Preferably, the hydrophobic solvent stabilizes the hydrophobic fraction such that at least 95% of the compounds in the hydrophobic fraction remain unchanged after at least 4 weeks.

While not limiting to the inventive subject matter, it is generally preferred that the hydrophobic solvent is or comprises methylene chloride, and that the hydrophilic solvent is or comprises water. In one exemplary use, the fresh plant materials comprise *Cannabis* plant materials or portions thereof, and the hydrophobic fraction comprises cannabinoids and optionally terpenoids.

In some embodiments, the hydrophobic solvent stabilizes the hydrophobic fraction such that at least 95% of the compounds in the hydrophobic fraction remain unchanged after at least 4 weeks, or after at least 3 months, or after at least 6 months. In other embodiments, the hydrophobic solvent stabilizes THC and/or CBD in the hydrophobic fraction such that at least 95% of the THC and/or CBD in the hydrophobic fraction remain unchanged after at least 3 months, or after at least 6 months. In still further embodiments, the step of storing the fresh plant materials is performed at controlled pressure and temperature wherein at least one of the pressure and temperature is distinct from ambient pressure and temperature.

Consequently, the inventor also contemplates an extraction vessel for extraction of a hydrophobic and a hydrophilic fraction of a fresh plant material. Preferred extraction vessels will include a storage container that contains a hydrophobic solvent as a bulk solvent and a hydrophobic solvent as a top layer solvent disposed above the hydrophobic solvent. A biomass container containing fresh plant materials is typically submerged in the bulk solvent below the top layer solvent. Preferably, the container has a removable cover that encloses the bulk solvent and the top layer solvent, and further has a solvent removal and a solvent replenishment port for the bulk solvent, and a skim port for the top layer solvent.

It is further generally preferred that the extraction vessel is fluidly coupled to a vacuum pump and a condenser, wherein the condenser is fluidly coupled to the vessel such as to return condensate to the storage container. In additional embodiments, the container is fluidly coupled to an evaporative unit to receive the hydrophobic solvent and to produce a crude oil, and a distillation unit and/or a winterizing unit are optionally fluidly coupled to the evaporative unit to receive the crude oil. In most cases, the extraction vessel is further coupled to a temperature control unit to maintain a temperature in the bulk solvent.

Various objects, features, aspects, and advantages will become more apparent from the following detailed description of preferred embodiments, along with the accompanying drawing in which like numerals represent like components.

DETAILED DESCRIPTION

The inventor has now discovered that various plant materials containing hydrophobic value products, and especially hemp and *Cannabis* plant materials, can be stored and preserved following harvest in a storage/processing system that will preserve the plant materials substantially 'as harvested' without the need for drying and immediate processing. Indeed, contemplated systems and methods will advantageously reduce microbial and/or chemical degradation that preserve compounds in the hydrophobic fraction over extended periods such as several weeks, and even several months. Moreover, contemplated systems and methods will produce a liquor that is enriched in a hydrophobic fraction (e.g., cannabinoids and/or terpenes) and that is depleted in a hydrophilic fraction (e.g., chlorophyll and flavonoids). The so formed liquor can then be removed from the storage/processing system and further processed to a final product such as a refined extract, or even single compounds at relatively high purity (e.g., >95% purity).

Consequently, it should be appreciated that the systems and methods presented herein will decouple plant harvest from any downstream processing steps and as such eliminate fluctuations in availability of raw materials as well as fluctuations in product quality. Indeed, it should be appreciated that the systems and methods presented herein will enable continuous production of downstream value components that is independent of the growing and/or harvesting cycles. Moreover, and as is described in more detail below, contemplated systems and methods will also avoid the need for drying the plant materials after harvest and before downstream processing. Still further, it should also be appreciated that the storage/processing system as presented herein will eliminate the need for drying the plant materials prior to extraction, and that freshly harvested plant materials (i.e., plant materials having no less than 50%, or no less than 70%, or no less than 85% water content relative to water content within 10 minutes of harvest) can be stored and extracted.

Figure 1:
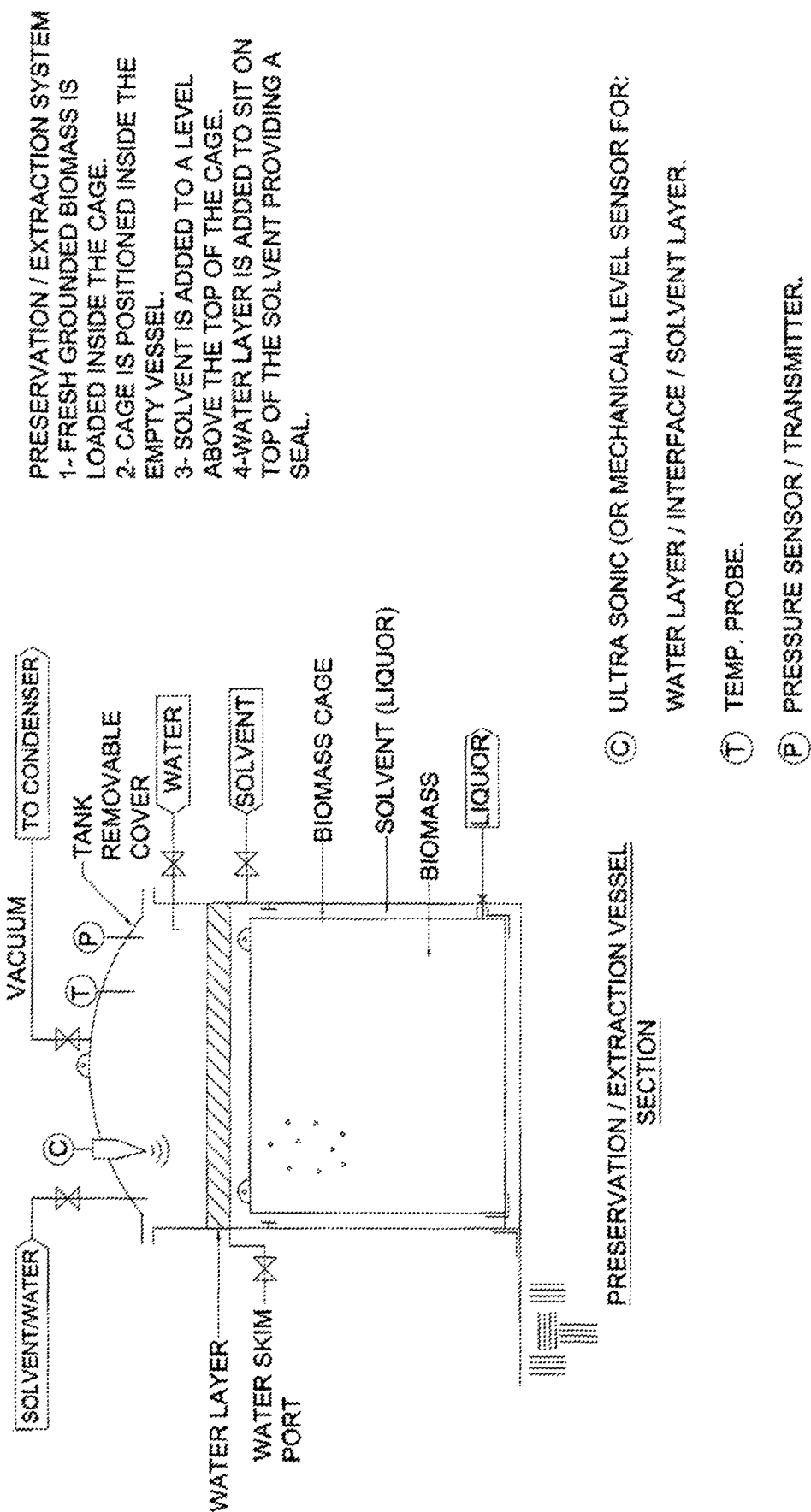
FIG. 1 depicts an exemplary configuration of a storage/extraction vessel according to the inventive subject matter.

One exemplary storage and/or extraction container for extraction of hydrophobic and hydrophilic fractions of plant materials is schematically illustrated in FIG. 1. Here, the storage and extraction container has a removable cover and encloses a biomass cage (e.g., wire cage) in which the plant materials are placed and retained. The storage and extraction container is partially filled with a hydrophobic solvent as a bulk solvent that covers the plant materials (and typically the biomass container). As will be readily appreciated, the biomass cage will allow the hydrophobic solvent in the storage and extraction container to penetrate the biomass present in the biomass cage. Therefore, the biomass cage may be configured as a wire or mesh basket, as a bag with a solvent permeable wall, or as a container with holes, slots, or otherwise shaped openings through which solvent can be exchanged.

Floating on top of the hydrophobic solvent is a relatively thin layer of a hydrophilic solvent that is immiscible with the hydrophobic solvent (e.g., no more than 1%, or no more than 0.1%, or no more than 0.05%, or no more than 0.01%, or no more than 0.001% of the hydrophilic solvent will dissolve in the hydrophobic solvent). In a typical embodiment, the thin layer of the hydrophilic solvent will continuously cover the hydrophobic solvent, and may have a thickness of at least 1 cm, or at least 5 cm, or at least 10 cm, or at least 20 cm to so provide a stable barrier layer that will prevent evaporation of the hydrophobic solvent (and any compounds dissolved therein) and/or oxygen ingress into the hydrophobic solvent. As can be seen from FIG. 1, the storage and extraction container will include various ports to remove and add hydrophilic and/or hydrophobic solvents, and the removable cover will further include various sensors for measuring environmental parameters such as pressure, temperature, solvent levels, etc. In still further contemplated aspects, the headspace over the layer of the hydrophilic solvent may be at least partially evacuated using a vacuum pump and condenser that will condense any solvent and return the condensate to the container. Where desired, the container may include further implements to impart any desired function, including heating and/or cooling elements, one or more agitators (e.g., impeller, ultrasound transducer, etc.), side draws, chemical sensors, etc.

Thus, it should be appreciated that the storage and extraction container will present a closed system that allows for hydrophobic solvent recycling of condensate and feeding of hydrophobic solvent returned from downstream processing (and addition of fresh/make-up hydrophobic solvent), as well as for removal of some of the hydrophilic solvent. Thus, it should be appreciated that the liquor (i.e., hydrophobic solvent containing extracted oils such as cannabinoids and/or terpenoids) can be removed from the container after any desirable point in time of storage (e.g., after 1 month, 2 months, 3 months, 6 months and even longer) for processing in which the extracted oils are separated from the hydrophobic solvent that can then be fed back to the container. In that way, serial or sequential extraction is contemplated that can use the same or different hydrophobic solvents. Moreover, newly harvested fresh plant material can be added at any time as is described in more detail below.

Figure 2:
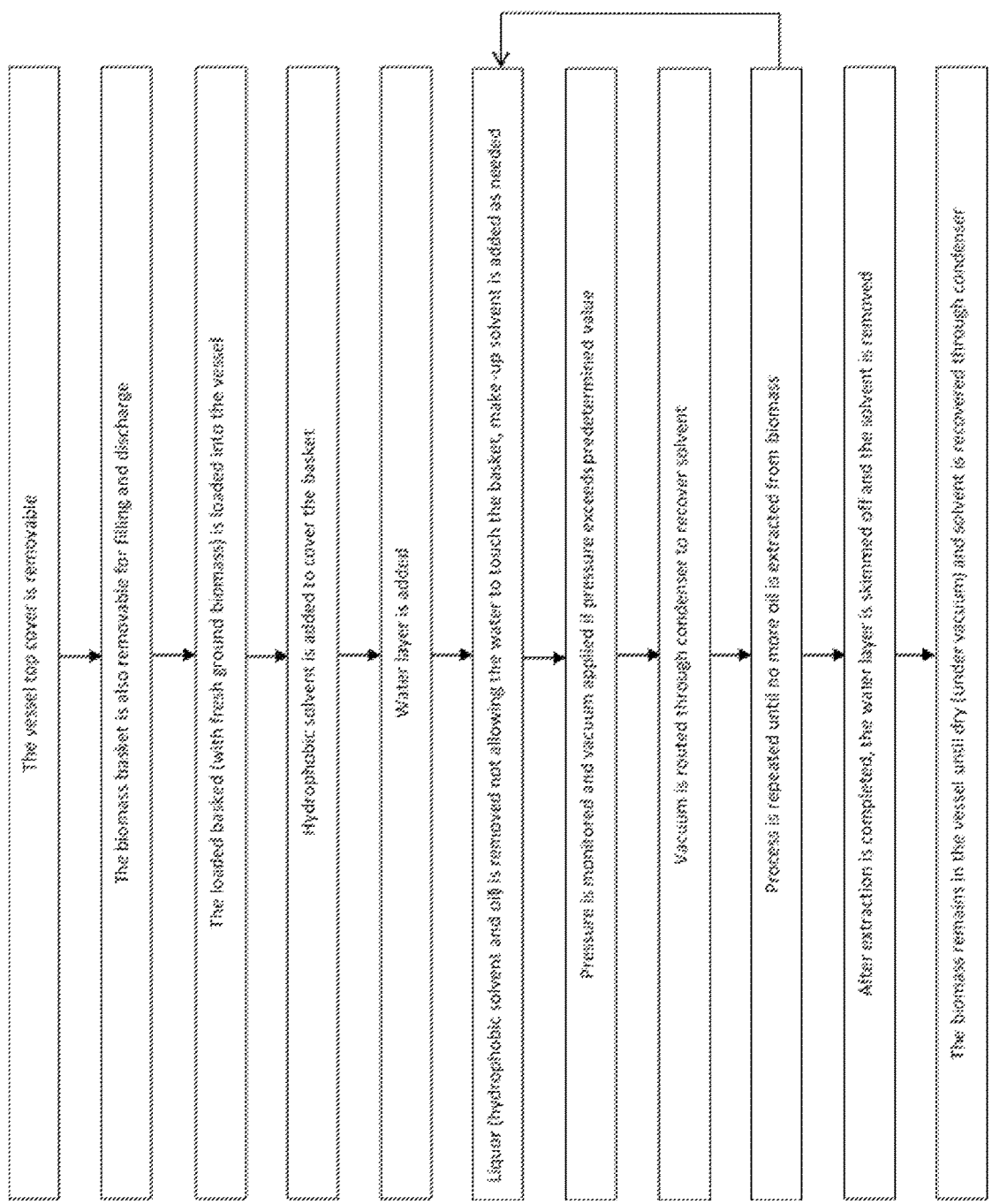
FIG. 2 depicts exemplary process steps for storage and extraction of THC, CBD, and/or terpenoids according to the inventive subject matter.

One exemplary process flow is shown in FIG. 2. Here, the storage and extraction container of FIG. 1 is used, and the plant material is freshly harvested and comminuted hemp or *Cannabis* (with an average largest dimension of hemp/*Cannabis* particles of between 0.5 cm and 5 cm). In an initial step, the removable cover is lifted and removed from the container and the biomass cage is filled with the freshly harvested and comminuted hemp or *Cannabis*. Of course, the biomass may also be further packaged into solvent permeable bags or other structures that are then placed into the biomass cage. The biomass cage is then closed with a lid such as to avoid floating of the comminuted hemp or *Cannabis* materials. Of course, it should be appreciated that while hemp and/or *Cannabis* plant materials are used as examples herein, numerous other plant materials such as herbs, spices, fruit, and vegetables (and portions or even extracts thereof) are also deemed suitable for use herein so long as such plant materials contain at least one hydrophobic valuable product (e.g., terpenoid, lipid, etc.). After placement of the filled biomass cage into the storage and extraction container, methylene chloride is added as the hydrophobic solvent in an amount sufficient to cover the biomass in the biomass container. Deionized water as hydrophilic solvent is then added on top of the methylene chloride to a height of about 10 cm to form an aqueous barrier layer. As needed or desired, additional plant material may be added to the storage and extraction container. Most typically, such addition can be performed by withdrawing the hydrophilic solvent from the container, lifting the biomass container out of the hydrophobic solvent, and adding (or replacing old biomass with) new biomass. The so re-filled biomass container is then again submerged into the hydrophobic solvent and the layer of hydrophilic solvent is restored.

As needed, the headspace over the hydrophilic solvent can be evacuated via a vacuum pump, and any solvent in the vapor phase can be condensed and routed back to the container. Of course, it should be appreciated that the hydrophobic solvent can be withdrawn at any desired rate from the container (and optionally new or recycled hydrophobic solvent is added to replenish) for downstream processing. In most typical aspects of downstream processing, the extracted hydrophobic valuables (e.g., cannabinoids and/or terpenoids) are separated from the hydrophobic solvent via distillation, selective solvent extraction, one or more chromatographic methods, solvent evaporation etc. Depending on the amount of plant material added, hydrophobic solvent used, and time of the biomass spent in the hydrophobic solvent, it should be appreciated that the biomass may be exposed to multiple subsequent charges of hydrophobic solvent, and that each charge may be processed in a downstream process (same or different process).

It should be noted that where fresh (or partially dried) plant material is used, contemplated systems and methods will also assist in extracting hydrophilic components from the plant materials as these (including water from the plant material) are immiscible with the hydrophobic solvent and will accumulate in the layer of hydrophilic solvent. Thus, and viewed from a different perspective, drying of the plant materials can not only be partially or entirely avoided, but various undesirable hydrophilic components are also removed/extracted during storage that advantageously produces a liquor that is enriched in hydrophobic components of the plant material. Such removal is especially advantageous as the extracted materials are substantially free or have a significantly reduced quantities of hydrophilic components that would otherwise require their removal in conventional methods. Notably, many of these hydrophilic components are often thermally unstable (e.g., chlorophyll, polyphenols, etc.) and tend to quickly react with other components and oxygen to form undesirable by-products that would taint the desired hydrophobic value products or that would render purification of the desired hydrophobic value products more difficult.

Once the storage and/or extraction process is concluded, it should be appreciated that the plant material (after removal of the hydrophilic and hydrophobic solvents from the container) can remain in the container and can be dried using heat and/or vacuum. Any residual solvent in the vapor phase can advantageously be condensed, recovered, and reused in the process.

It should also be recognized that the hydrophobic components in the hydrophobic solvent (in the container and after removal from the container) will impart significant storage stability to the plant materials and extracted hydrophobic value products against microbial and/or chemical degradation (e.g., oxidation, decarboxylation, etc.). Most typically, and as described in more detail, it is contemplated that at least 85%, or at least 90%, or at least 95% of the compounds in the hydrophobic fraction remain unchanged after at least 4 weeks, or after at least 3 months, or after at least 6 months. Thus, it is also contemplated that at least 85%, or at least 90%, or at least 95% of the THC, CBD, and/or terpenoids in the hydrophobic fraction remain unchanged after at least 3 months, or after at least 6 months. Such storage stability allows for extended periods of processing without loss of product quality.

As will be readily appreciated, the liquor from the container can be subjected to a number of downstream processes, and the person of ordinary skill in the art will be readily apprised of a suitable choice, depending on the particular desired end product (e.g., crude extract, winterized extract, complex extract, purified CBD, purified THC, mixture of terpenoids, isolated terpenoids, etc.). In most cases, however, the liquor from the container will be subjected to an evaporative process, for example, using a rotational evaporator, a falling film evaporator, etc. in which the removed hydrophobic solvent is preferably recovered, and then recycled/reused in the system. Such recycling or reuse can be direct or indirect using a surge or storage tank. The so obtained crude oil may then be winterized, fractionally distilled and/or extracted, subjected to various chromatographic steps (e.g., reversed phase chromatography, flash chromatography, etc.) to produce a product with desired specification. Among other choices, suitable processing methods for the crude oil include those described in co-pending US application with the Ser. No. 17/191,565, which is incorporated by reference herein in its entirety.

Suitable plant materials are typically freshly harvested plant materials, however, partially dried (e.g., residual water content of at least 70 wt %, or at least 50 wt %, or at least 30 wt %) or completely dried (e.g., dried to constant weight) plant materials are also deemed suitable for use herein. It is further generally contemplated (but not required) that the plant materials will be comminuted or otherwise partially disintegrated to increase (surface) contact with the hydrophobic solvent and facilitate extraction of hydrophobic contents. To that end, the plant materials may be chopped, crushed, or otherwise comminuted, or only select plant portions such as leaves, flowers, and/or buds may be used (which may also be subject to further comminution). As noted earlier, the plant material is placed in the biomass cage and can be covered with a screen, lid or other cover to prevent the materials from floating in the solvent. Likewise, the (comminuted) biomass can be placed in a pouch, bag, or other container that is permeable to the hydrophobic solvent.

With respect to suitable solvents, it is generally contemplated that the solvents are generally immiscible (e.g., no more than 1%, or no more than 0.1%, or no more than 0.05%, or no more than 0.01%, or no more than 0.001% of the hydrophilic solvent will dissolve in the hydrophobic solvent), and that the hydrophobic solvent has a higher density than the hydrophilic solvent. Most preferably at least one, and more typically both solvents are non-flammable and/or non-toxic. It is also further preferred, but not required, that the hydrophobic solvent has a boiling point at or below 100° C., or at or below 80° C., or at or below 50° C. Therefore, especially preferred solvents include methylene chloride as the hydrophobic solvent and water as the hydrophilic solvent.

However, numerous alternative hydrophobic solvents are also contemplated, and suitable solvents will include single solvents and solvent mixtures such as non-flammable mixtures of compounds based on halogenated hydrocarbons (e.g., 65% to 85%), highly polar compounds such as various R—OH (alcohol) or R(=O)—R" (ketone) (e.g., 5% to 10%) and R—O—R' (ether) (e.g., 7% to 18%). Advantageously, such solvents and solvent mixtures will assist in removing all water-soluble compounds, which will enrich in the hydrophilic solvent that forms the top layer above the hydrophobic solvent. As will be readily understood by the skilled artisan, suitable mixtures will be determined by the affinity of the Hansen Parameters (Polar, Hydrogen Bonding and Dispersion Solubility parameters) to the target desired compounds to partition into the hydrophilic and/or hydrophobic phases. It is also preferred that where the hydrophobic solvent is a mixture, the mixture is an azeotropic mixture that is preferably non-flammable. Where desired, the solvent may be exposed to an electric field by immersing copper and titanium electrodes at about 24-35 V at a frequency of about 60 Hz to promote a "polarity alignment" in the solvent prior to use.

Similarly, suitable hydrophilic solvents will typically be polar or dipolar aprotic and will preferably be hydrogen bond donors or acceptors. Therefore, especially suitable hydrophilic solvents include water, short chain alcohols (e.g., $C_1$-$C_4$), acetic acid, acetone, dimethyl sulfoxide, dimethyl formamide, etc. In this context, it should be appreciated that the hydrophilic solvent will generally act as a top layer solvent that due to its lower density will cover the entire upper surface of the hydrophobic solvent that acts as the bulk solvent (i.e., the solvent into which one or more value products are dissolved and that is processed in a downstream operation to recover the value product(s)). It should be noted, however, that in certain embodiments the nature of the bulk solvent and the top layer solvent may be switched (i.e., hydrophilic bulk solvent and hydrophobic top layer solvent) where the value components are hydrophilic.

With respect to the storage/extraction container, it should be appreciated that the volume of the container is not limiting to the inventive subject matter, and that all volumes are deemed suitable for use herein. However, in most typical embodiments, the volume of the container will be at least 10 L, or at least 100 L, or at least 500 L, or at least 1,000 L, and even larger. Therefore, suitable biomass cages will have a size and dimension to fit into the container and to accommodate a desirable plant material in a form as harvested, in comminuted form, or in a form where one or more plant components have been removed (e.g., roots, stems, etc.). Among other contemplated examples, the biomass cage may be a wire cage, a cage with openings that allow retention of the plant materials while enabling access of the hydrophobic solvent. Therefore, the term 'cage' as used herein includes both rigid containers such as metallic crates as well as non-rigid containers such as bags and sacks. Where the density of the biomass cage with the biomass contained therein is less than the density of the hydrophobic solvent, a retention mechanism such as a weight, anchor, or lid-like structure may be used to maintain the cage fully immersed or submerged in the hydrophobic solvent.

In still further contemplated embodiments, it should be appreciated that the container as described herein is suitable for both continuous and discontinuous operation, which is particularly advantageous where biomass availability is irregular (e.g., due to growth or harvest seasons or cycles), or where the biomass availability exceeds processing capacity of an associated processing facility or equipment. Likewise, where the solvent extraction is a relatively lengthy process, or where the extraction uses two or more different hydrophobic solvents, discontinuous operation can be implemented. Thus, withdrawal of the liquor from the container may be continuous, in intervals with volumes withdrawn that are less than the entire volume, or batch-wise where the entire volume is withdrawn. Replenishment of the hydrophobic solvent with fresh (same or different) hydrophobic solvent or hydrophobic solvent recovered from a downstream isolation process that separates the value product form the hydrophobic solvent is therefore expressly contemplated.

EXAMPLES

In the laboratory, hemp and *Cannabis* materials have been treated using this method in both the fresh state and dried material. For example, in one representative process small samples of 500 g were placed in a 1,000 ml beaker with around 700 ml of solvent. The solvent used was 94% v/v Methylene Chloride, 4% v/v Acetone and 2% v/v ethanol for the hydrophobic phase. The hydrophilic phase was made of 35 ml of water and placed over the hydrophobic phase. The sample material was pressed to the bottom of the beaker using a stainless-steel metal mesh that was left in the beaker throughout the experiment. The hydrophobic solvent layer stayed clear above the plant material level. The interphase level was marked as well as the top water layer level. Water was added as the water level went down. The interphase level was expected to remain constant, and after 6 weeks did not change. There was no noticeable loss of solvent as the water formed a hermetic seal on top of the hydrophobic solvent. Registered temperatures in the room varied from 8° C. to 27° C. and at these temperatures no apparent loss of solvent was observed. The solvent was sampled regularly to produce samples of at least 1.00 g of crude oil. These samples were sent to the lab for quantification of CBD and THC contents. For at least 6 weeks it has been shown in the lab that the initial (first sample) content of THC/CBD remained uniform throughout the test for at least the term of these tests (6 weeks). Both dried and fresh materials showed the same behavior in the curve concentration vs. time for the total period of the test.

In a longer-term study, the inventor sought to establish that fresh cut material can be preserve for time periods of 6 months (~180 days), and well beyond 6 months (about 2 years), and that after this period all the valuable cannabinoids, lipids, waxes, and terpenes can be extracted with the same quality as if extracted right after harvesting the plant as is shown in more detail below. Further testing also demonstrated that loss of solvent was either negligible or minimal and did not affect the economics of the process. Finally, the inventor determined the saturation level of the crude oil/solvent liquor extracted at different stages of the process. To that end, an industrial scale test was implemented that used large amounts of hemp plant material (about 2,800 lbs.) and large quantities of solvent (about 750 gal.)

More specifically, a double containment tank was used as the storage/extraction vessel, with the double containment providing the required safety in case of a spill. 2,800 lbs. of hemp were bought from a greenhouse farm in Ventura, California. The hemp was harvested, ground, and put inside burlap bags in the tank on the same day, and sandbags were used to prevent the hemp bags from floating in the solvent. The bags containing the hemp were placed inside the tank in an orderly manner to fill up the space.

An interface level indicator system was designed to accurately measure the level of the solvent/water interface and to indicate the top water level. Here, two stainless steel floats were used with their indicating rods are set in a coaxial manner. The bottom float was weighed and measured. The Archimedes principle was used to calculate the required mass needed in the float to compensate the two liquids buoyancy upward force exerted in the float. Lead shot was added inside the float to make it sink in water and float in the solvent. Samples of the plant were also sent to a contracting lab for analytical tests to determine their CBD and other cannabinoids content in their fresh and dried form.

The two levels were recorded daily to follow up on evaporation rates both in water and solvent. A stainless-steel tank was also set from the top of the tank to the bottom of it and it was fitted with a #300 strainer. This line was used to draw weekly samples of the liquor (2 liters) that were used to determine the solvent saturation level and to determine the saturation level time behavior. These same samples extracted the crude oil and were sent for analytical testing to determine the cannabinoid profile and potency concentration in the crude oil.

Monthly samples of 20 liters of liquor were tested for the quantity and quality of the distillate and helped ascertain that these were kept constant during the testing protocol. The test was started on Jan. 27, 2020. The materials were harvested, ground, and transported to the inventor's facility. There they were put in bags and set inside a 1,000 gal tank. 14 drums of solvent were also added yielding about 770 gal. of solvent. Exemplary laboratory test results are shown in Tables 1-7, with Table 1 depicting total CBD and THC concentrations over time.

TABLE 1

| No. | Sample ID | Sample Description | Date Collection | Date Testing | Total CBD % | Total THC % |
|---|---|---|---|---|---|---|
| 1 | 169937 | RAW FLOWER WET | 27, Jan. 20 | 30, Jan. 20 | 2.969% | N/D |
| 2 | 200211BLF | RAW FLOWER DRY | 27, Jan. 20 | 11, Feb. 20 | 13.000% | 0.400% |
| 3 | 200211PCC1 | CRUDE FIRST WEEK | 4, Feb. 20 | 11, Feb. 20 | 43.000% | 1.700% |
| 4 | PCC-2P | CRUDE 4 MO | | 27, May 20 | 85.4% | 4.2% |
| 5 | PCC-1P | CRUDE 4 MO | | 27, May 20 | 79.1% | 4.5% |
| 6 | PCC-3P | CRUDE 4 MO | | 27, May 20 | 88.0% | 3.5% |
| 7 | PCC 12-10 | CRUDE 23 MO | | 20, Dec. 21 | 62.92% | 13.01 |

Table 2 shows an exemplary composition for 200211BLF at 11 Feb. 2020

TABLE 2

| Cannabinoids | Potency Percent | Potency by weight |
|---|---|---|
| CBDV | — | — |
| CBDA | 13.0% | 129.91 mg/g |
| CBG | — | — |
| CBD | 0.3% | 2.71 mg/g |
| THCV | — | — |

TABLE 2-continued

| Cannabinoids | Potency Percent | Potency by weight |
|---|---|---|
| CBN | — | — |
| d9 THC | — | — |
| d8 THC | — | — |
| CBC | — | 0.33 mg/g |
| THCA-A | 0.4% | 3.79 mg/g |
| | | 136.74 mg/g |

Table 3 shows an exemplary composition for 200211PCC1 at 11 Feb. 2020

TABLE 3

| Cannabinoids | Potency Percent | Potency by weight |
|---|---|---|
| CBDV | 0.1% | 1.08 mg/g |
| CBDA | 34.5% | 344.77 mg/g |
| CBG | 0.3% | 2.55 mg/g |
| CBD | 8.3% | 82.88 mg/g |
| THCV | — | — |
| CBN | — | — |
| d9 THC | 0.8% | 8.16 mg/g |
| d8 THC | — | — |
| CBC | 0.7% | 7.05 mg/g |
| THCA-A | 0.9% | 9.17 mg/g |
| | | 455.66 mg/g |

Table 4 shows an exemplary composition for PCC-2P at 27 May 2020

TABLE 4

| Cannabinoids | Potency Percent | Potency by weight |
|---|---|---|
| CBDV | 0.5% | 4.55 mg/g |
| CBDA | — | — |
| CBG | 0.8% | 7.65 mg/g |
| CBD | 84.9% | 848.70 mg/g |
| THCV | — | — |
| CBN | 0.2% | 1.75 mg/g |
| d9 THC | 4.2% | 42.14 mg/g |
| d8 THC | — | — |
| CBC | 2.5% | 24.98 mg/g |
| THCA-A | — | — |
| | | 929.77 mg/g |

Table 5 shows an exemplary composition for PCC-1P at 27 May 2020

TABLE 5

| Cannabinoids | Potency Percent | Potency by weight |
|---|---|---|
| CBDV | 0.8% | 8.03 mg/g |
| CBDA | — | — |
| CBG | 1.1% | 11.29 mg/g |
| CBD | 78.3% | 783.05 mg/g |
| THCV | — | — |
| CBN | 0.1% | 1.03 mg/g |
| d9 THC | 4.5% | 44.63 mg/g |
| d8 THC | — | — |
| CBC | 2.4% | 23.78 mg/g |
| THCA-A | — | — |
| | | 871.80 mg/g |

Table 6 shows an exemplary composition for PCC-3P at 27 May 2020

TABLE 6

| Cannabinoids | Potency Percent | Potency by weight |
|---|---|---|
| CBDV | 0.4% | 4.10 mg/g |
| CBDA | — | — |
| CBG | 0.5% | 4.77 mg/g |
| CBD | 87.6% | 875.96 mg/g |
| THCV | — | — |
| CBN | 0.1% | 1.04 mg/g |
| d9 THC | 3.5% | 35.04 mg/g |
| d8 THC | — | — |
| CBC | 2.6% | 26.16 mg/g |
| THCA-A | — | — |
| | | 947.07 mg/g |

Table 7 shows an exemplary composition for PCC 12-10 at 20 Dec. 2020

TABLE 7

| Analyte | LOD (mg/g) | LOQ (mg/g) | Result (%) | Result (mg/g) |
|---|---|---|---|---|
| THCa | 0.04 | 0.987 | ND | ND |
| Δ9-THC | 0.077 | 0.987 | 13.0101 | 130.101 |
| Δ8-THC | 0.055 | 0.987 | 2.4087 | 24.087 |
| THCV | 0.088 | 0.987 | 0.1085 | 1.085 |
| CBDa | 0.043 | 0.987 | ND | ND |
| CBD | 0.111 | 0.987 | 62.923 | 629.23 |
| CBDV | 0.077 | 0.987 | 0.2719 | 2.719 |
| CBN | 0.038 | 0.987 | 0.4668 | 4.668 |
| CBGa | 0.077 | 0.987 | ND | ND |
| CBC | 0.057 | 0.987 | 0.734 | 7.34 |
| Total THC | | | 13.0101 | 130.101 |
| Total CBD | | | 62.923 | 629.23 |
| Total | | | 79.923 | 799.23 |

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of storing and processing plant materials, comprising:
   providing a two-layer solvent system comprising a hydrophobic solvent and a hydrophilic solvent, wherein the hydrophilic solvent is less dense than the hydrophobic solvent;
   implementing the two-layer solvent system in a storage container that contains the hydrophobic solvent as a bulk solvent and the hydrophilic solvent as a top layer solvent disposed above the hydrophobic solvent;
   placing fresh plant materials in a biomass cage that is configured to allow the bulk solvent to enter into and exit from the biomass cage, and submerging the biomass cage in the bulk solvent below the top layer solvent such that the fresh plant materials are in contact with the bulk solvent;
   storing the fresh plant materials in the biomass container for a time sufficient to dissolve a hydrophobic component of the plant materials to dissolve in the bulk solvent and to dissolve a hydrophilic component to dissolve in the top layer solvent;
   removing at least some of the bulk solvent containing the hydrophobic component, and separating the hydrophobic component from the bulk solvent to produce recycled hydrophobic solvent; and
   using the recycled hydrophobic solvent as bulk solvent.

2. The method of claim 1, wherein the recycled hydrophobic solvent is used as the bulk solvent while storing the plant materials in the biomass cage.

3. The method of claim 1, wherein separating the hydrophobic component from the bulk solvent comprises distillation, selective solvent extraction, a chromatographic separation, or solvent evaporation.

4. The method of claim 1, further comprising the steps of closing the storage container, applying a vacuum to a head space of the container to produce a vapor stream, recovering at least some of the hydrophilic and/or hydrophobic solvent from the vapor stream, and feeding the recovered hydrophilic and/or hydrophobic solvent back into the container.

5. The method of claim 1, further comprising a step of removing a portion of the top layer solvent while storing the plant materials in the biomass cage.

6. The method of claim 1, further comprising a step of placing additional fresh plant materials in the biomass cage while the initial fresh plant materials are stored in the biomass cage.

7. The method of claim 1, wherein the biomass cage is configured as a closed mesh or wire basket, a bag with walls that are permeable to the bulk solvent, or a closed container with a plurality of openings that allow bulk solvent exchange.

8. The method of claim 1, wherein the hydrophobic solvent comprises a non-flammable halogenated hydrocarbon, a polar solvent, and/or an ether, and wherein the hydrophilic solvent comprises water.

9. The method of claim 1, wherein the hydrophobic component comprises a cannabinoid and/or terpenoid.

10. The method of claim 1, wherein the fresh plant materials comprise *Cannabis* plant materials, hemp plant materials, herbs, spices, fruit, or vegetables, or portions thereof.

11. The method of claim 1, wherein the fresh plant materials are stored in the biomass container for at least 3 months.

12. The method of claim 1, wherein the hydrophobic solvent stabilizes the hydrophobic component such that at least 95% of the compounds in the hydrophobic component remain chemically unchanged after at least 4 weeks.

13. The method of claim 1, wherein the hydrophobic solvent stabilizes the hydrophobic component such that at least 95% of the compounds in the hydrophobic components remain chemically unchanged after at least 3 months.

14. The method of claim 1, wherein the hydrophobic component comprises THC, CBD, and/or terpenoids, and wherein the hydrophobic solvent stabilizes THC, CBD, and/or terpenoids such that at least 95% of the THC, CBD, and/or terpenoids in the hydrophobic solvent remain chemically unchanged after at least 3 months.

15. The method of claim 1, wherein the step of storing the fresh plant materials is performed at controlled pressure and temperature, and wherein at least one of the pressure and temperature is distinct from ambient pressure and temperature.

* * * * *